US012618234B1

(12) United States Patent
    Alhamli

(10) Patent No.: US 12,618,234 B1
(45) Date of Patent: May 5, 2026

(54) HAND AND FOOT SINK APPARATUS

(71) Applicant: Mossab M M J Alhamli, Al Asima (KW)

(72) Inventor: Mossab M M J Alhamli, Al Asima (KW)

( * ) Notice: Subject to any disclaimer, the term of this patent is extended or adjusted under 35 U.S.C. 154(b) by 0 days.

(21) Appl. No.: 19/179,706

(22) Filed: Apr. 15, 2025

(51) Int. Cl.

| | |
|---|---|
| *E03C 1/01* | (2006.01) |
| *A47K 5/12* | (2006.01) |
| *A47K 7/02* | (2006.01) |
| *A47K 10/48* | (2006.01) |
| *A61L 2/10* | (2026.01) |
| *A61L 2/26* | (2006.01) |
| *E03C 1/18* | (2006.01) |
| *E03C 1/326* | (2006.01) |

(52) U.S. Cl.
    CPC .............. *E03C 1/01* (2013.01); *A47K 5/1217* (2013.01); *A47K 7/026* (2013.01); *A47K 10/48* (2013.01); *A61L 2/10* (2013.01); *A61L 2/26* (2013.01); *E03C 1/18* (2013.01); *E03C 1/326* (2013.01); *A47K 2210/00* (2013.01); *A61L 2202/14* (2013.01)

(58) Field of Classification Search
    CPC ..... E03C 1/01; E03C 1/16; E03C 1/18; E03C 1/326; E03C 2201/30; A47K 5/1217; A47K 7/026; A47K 10/48; A61L 2/26; A61L 2/10; A61L 2202/14
    USPC ........... 4/661, 663–665, 622, 546, 548, 553
    See application file for complete search history.

(56) References Cited

U.S. PATENT DOCUMENTS

| | | | |
|---|---|---|---|
| 1,616,313 | A | 2/1927 | Farmer |
| 9,187,882 | B2 | 11/2015 | Masoud |
| 2015/0052676 | A1 | 2/2015 | Azmi |

FOREIGN PATENT DOCUMENTS

| | | | | |
|---|---|---|---|---|
| CN | 201398911 Y | 2/2010 | | |
| CN | 102776933 A | 11/2012 | | |
| CN | 212815982 U | 3/2021 | | |
| GB | 2314015 B | 2/1999 | | |
| GB | 2500201 A | * 9/2013 | ............... | E03C 1/01 |
| JP | H0813296 B2 | 2/1996 | | |
| JP | 2005142519 A | * 6/2005 | | |
| KR | 200323944 Y1 | * 8/2003 | ............. | A47K 7/026 |
| KR | 100573286 B1 | * 4/2006 | ............... | E03C 1/18 |

OTHER PUBLICATIONS

"WuduWash Dual Level Wudu Basin 2.0 Large Foot Wash Deep Sink Ablution With Tap", Etsy, published on Oct. 29, 2024.

* cited by examiner

*Primary Examiner* — Tuan N Nguyen
(74) *Attorney, Agent, or Firm* — Nath, Goldberg & Meyer; Joshua B. Goldberg

(57) ABSTRACT

A hand and foot sink apparatus, comprising a housing having a top end and an opposing bottom end, the housing including a hand sink disposed at the top end of the housing and including a basin, a faucet, and a drain, and a foot sink disposed within a first opening along a side portion of the housing below the hand sink. The foot sink is partially enclosed within the housing and includes a basin, a plurality of sprayers, and a footrest. The housing includes one or more nozzles configured to dispense soap, and one or more supply holders configured to store one or more containers of soap, the one more containers of soap being connected to the one or more nozzles through conduits. One or more controls of the housing are configured to operate the one or more nozzles.

14 Claims, 6 Drawing Sheets

HAND AND FOOT SINK APPARATUS

BACKGROUND

Technical Field

The disclosure of the present patent application relates to a personal hygiene washing appliance. More specifically, the invention is a dual sink for washing hands and feet of a user, with separate basins for each.

Background Art

In some customs and religions, it is a ritual to clean both one's hands and feet before prayer. Others may want to wash their feet for sanitary purposes such as when coming back home from the outdoors or when taking their shoes and socks off etc. It is both difficult and unsanitary to wash feet in the same sink where hands are washed.

Therefore, it is desirable to have an apparatus that includes both a hand washing sink and a foot washing sink.

SUMMARY

An embodiment of the present disclosure is directed to a hand and foot sink apparatus, including an apparatus housing having a top end and an opposing bottom end, the apparatus housing including a hand sink disposed at the top end of the apparatus housing and including a basin, a faucet, and a drain, and a foot sink disposed within a first opening along a side portion of the apparatus housing below the hand sink. In an embodiment, the foot sink is partially enclosed within the apparatus housing and includes a basin, a plurality of sprayers, and a footrest, the footrest being disposed in the basin. In an embodiment, the apparatus housing includes one or more nozzles configured to dispense soap, and one or more supply holders configured to store one or more containers of soap, the one more containers of soap being connected to the one or more nozzles through conduits. In an embodiment, one or more controls of the apparatus housing are configured to operate the one or more nozzles.

According to another embodiment, a hand and foot sink apparatus includes an apparatus housing having a top end and an opposing bottom end, the apparatus housing including a hand sink disposed at the top end of the apparatus housing and including a basin, a faucet, and a drain, a foot sink disposed within a first opening along a side portion of the apparatus housing below the hand sink. In an embodiment, the foot sink is partially enclosed within the apparatus housing and includes a basin, a plurality of sprayers, and a footrest, the footrest being disposed in the basin. In an embodiment, the apparatus housing includes one or more nozzles configured to dispense soap, and one or more supply holders configured to store the one or more containers of soap, the one more containers of soap being connected to the one or more nozzles through conduits. In an embodiment, the apparatus housing includes a first pair of blowers proximate the top end of the apparatus housing and under the hand sink, one or more UV lights directed toward the foot sink, and one or more controls configured to operate the one or more nozzles and the first pair of blowers.

According to another embodiment, a hand and foot sink apparatus includes an apparatus housing having a top end and an opposing bottom end, the apparatus housing including a hand sink disposed at the top end of the apparatus housing, the hand sink including a basin, a faucet, and a drain, a foot sink disposed within a first opening along a side portion of the apparatus housing below the hand sink. In an embodiment, the foot sink is partially enclosed within the apparatus housing and includes a basin, a plurality of sprayers, and a footrest, the footrest being disposed in the basin. In an embodiment, apparatus housing includes one or more nozzles configured to dispense soap and one or more supply holders configured to store the one or more containers of soap, the one or more containers of soap being connected to the one or more nozzles through conduits. In an embodiment, the footrest includes a footrest housing having a lid with openings defined therethrough, the lid being configured to selectively close the footrest housing. In an embodiment, the apparatus housing includes a removable footrest removably secured within a second opening of the apparatus housing and below the foot sink, a first pair of blowers proximate the top end of the apparatus housing and under the hand sink, and a second pair of blowers proximate the foot sink, and one or more controls configured to operate the one or more nozzles, and the blowers.

These and other features of the present subject matter will become readily apparent upon further review of the following specification.

DETAILED DESCRIPTION

Figure 1:
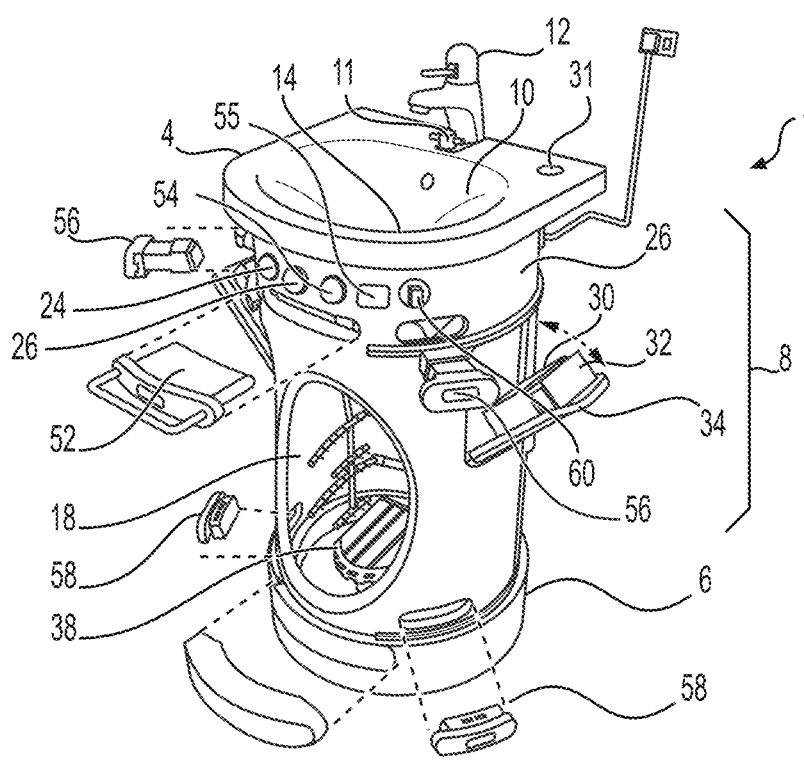
FIG. 1 is an exploded view of an embodiment of a hand and foot sink apparatus as described herein.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Where a range of values is provided, for example, length ranges, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The present disclosure relates to a hand and foot sink apparatus including an apparatus housing having a hand sink at a top end thereof and a foot sink disposed within a first opening along a side of the apparatus housing. The hand sink includes a basin with a drain and a faucet. Controls on the apparatus housing can be manipulated to operate the hand sink and the foot sink. The foot sink is disposed in a lower portion of the apparatus housing below the hand sink. The foot sink includes a plurality of sprayers, a footrest, and a sloped basin to allow for draining. The foot sink can be partially enclosed within the apparatus housing. The sprayers are configured to spray water into the basin towards the footrest upon which a foot of the user may be placed.

The water can flow from a water source, e.g., a water supply line, to the faucet of the hand sink and the sprayers of the foot sink. The water source for the foot sink may be the same water source for the faucet of the hand sink. Water from the water source may be directed to the hand sink and the foot sink through one pipe or through different pipes. In an embodiment, the water is directed to the hand sink and the foot sink through a single water pipe. The single water pipe can be connected to the faucet and to first and second water lines. Each of the first and second water lines include spray arms extending therefrom. Each of the spray arms can include ports or sprayers configured to spray water into the basin of the foot sink.

The apparatus housing may include at least one soap container, and a nozzle connected thereto for dispensing soap. In various embodiments, each soap container may contain a different type of soap. The different soaps may include a his and hers soap where each user in a household has a preferred soap. The selected soap may spray through all the nozzles and not only the nozzles on the same side of the selected soap container.

In an embodiment, the footrest 38 may be disposed within the foot sink 6 to receive a foot of a user thereon. The footrest 38 may be capable of moving in a front to back position. In a further embodiment ultraviolet (UV) lights may be located in the apparatus housing to sanitize the basin of the foot sink between uses.

Referring to FIG. 1, an exploded view of an embodiment of a hand and foot sink apparatus 2 is illustrated. The apparatus includes an apparatus housing 8 having a hand sink 4 at a top end thereof and a foot sink 6 at a bottom end thereof, below the hand sink 4. The hand sink 4 can be exposed at a top end of the apparatus housing 8, while the foot sink 6 is partially enclosed within an opening 18 at a side of the apparatus housing 8. The hand sink 4 includes a basin 10, a faucet 12, and a drain 14. In various embodiments, the hand sink 4 is configured for hand washing.

A user may divert water from the hand washing sink 4 to the sprayers on the foot sink 6 by pulling a lever 11. The water may then flow from the faucet 12 of the hand washing sink 6 down to the ports 22 of the spray arms 20 above the foot sink 6.

Buttons are included at a top end of the apparatus housing. The first button 24 controls the foot mat. The first button may be configured to move the footrest back and forth. The second button 26 may be electrically coupled with a first set and a second set of blowers. The third button 54 may start a self-sanitizing button function within the apparatus housing to clean and sanitize the foot sink.

Figure 2:
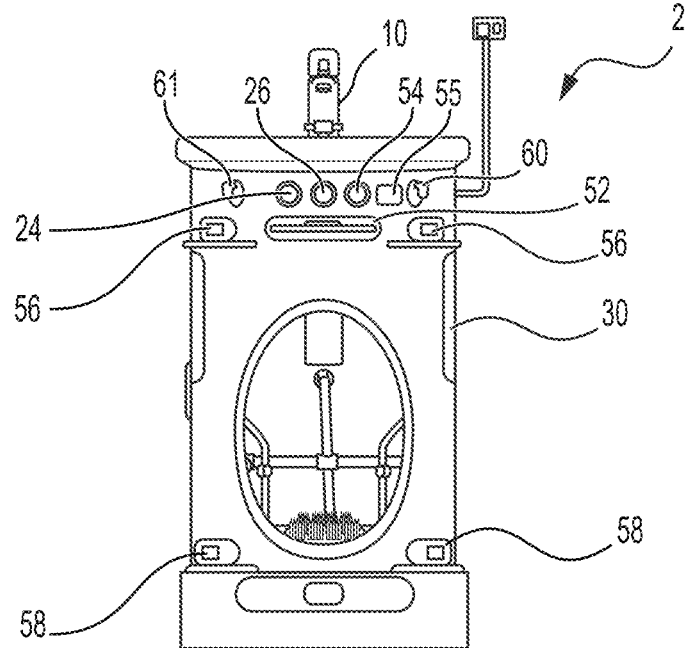
FIG. 2 is a front view of an embodiment of a hand and foot sink apparatus as described herein.
Figure 7:
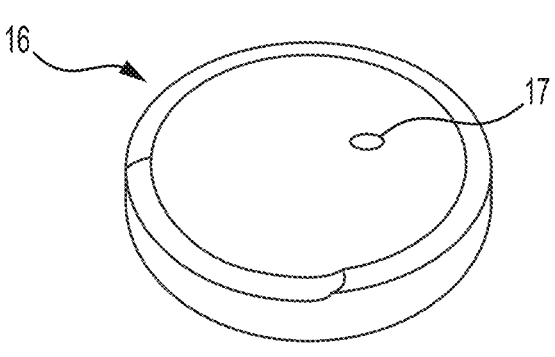
FIG. 7 is a perspective view of an embodiment of a sloped basin.

According to an embodiment, the foot sink 6 includes a sloped basin 16 having a drain 17, as illustrated in FIG. 7. The opening 18 can be curved inward toward the sloped basin 16. In various embodiments, the apparatus housing 8 may have a curved shape as illustrated in FIG. 1. In other embodiments, the apparatus housing 8 may have a rectangular shape as illustrated in FIG. 2.

In an embodiment, the water is directed to the hand sink 4 and the foot sink 6 through a single supply water pipe. The single supply water pipe can be connected to the faucet 12 of the hand sink 4. In an embodiment, the main water pipe can be connected to first and second water lines of the foot sink 6. Each of the first and second water lines of the foot sink 6 includes spray arms 20 with ports 22 that are configured to spray water into the basin of the foot sink 6, as illustrated in FIG. 6.

In various embodiments, the spray arms 20 with ports 22 are configured to spray a foot of a user that is positioned on footrest 38 of the foot sink 6. The spray arms 20 with ports 22 may also be used to clean the basin 16. The spray arms 20 with ports 22 may be controlled by a first set of controls 24 located on the apparatus housing 8, e.g., on a top edge 26 of the apparatus housing 8. The top edge 26 of the apparatus housing 8 may be under the basin 10 of the hand sink 4.

Figure 6:
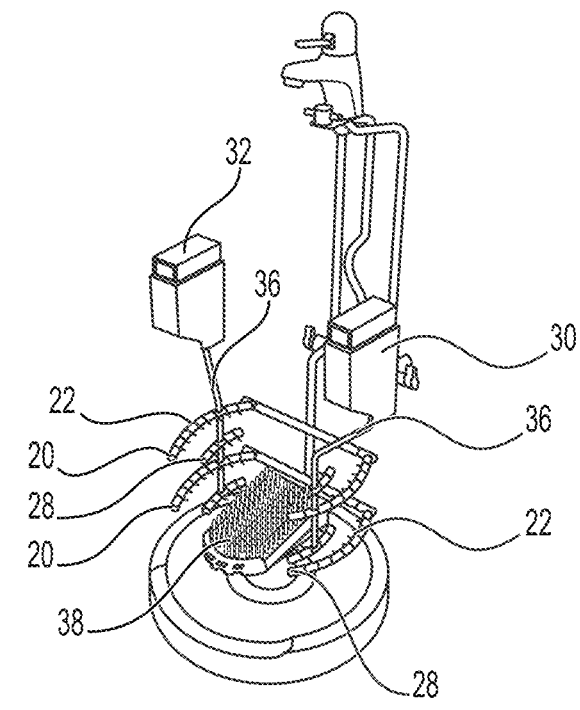
FIG. 6 is a view of an embodiment of a hand and foot sink apparatus without the apparatus housing and top portion.

Within the apparatus housing 8 are nozzles 28 connected to supply holders 30 through conduits 36, as illustrated in FIG. 6. In various embodiments, the supply holders 30 include liquid soap and the nozzles 28 are configured to dispense the soap to the user. The soap may be dispensed by a user with the controls 60 and 61. Each of the controls 60 and 61 can be used to independently dispense soap. For example, control 60 is for the soap container soap on the right side of the apparatus housing and control 61 is for soap container on the left side of the apparatus housing. In various embodiments, the soap bottles can be closer to a middle portion of the apparatus housing. As previously described, each soap container may contain a different type of soap. The different soaps may include a his and hers soap where each user in a household has a preferred soap. The selected soap may spray through all the nozzles and not only the nozzles on the same side of the selected soap container. In other embodiments, the nozzles 28 may spray other liquids such as, by non-limiting example, disinfecting liquids to clean the foot sink 6. The nozzles 28 are coupled with controls 60 and 61 located near the top of the apparatus housing 8.

In an embodiment, the supply holder 30 container of soap 32. The supply holder 30 may include a door 34 which can be opened to access the container 32. In various embodiments, an additional soap container may be located near the hand sink. The soap may be dispensed using a lever extending from the hand sink in the opening 31 as shown.

Figure 8:
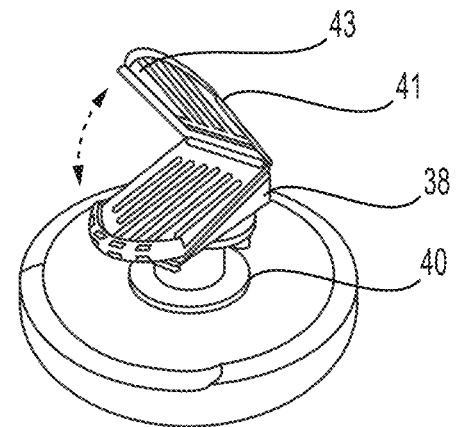
FIG. 8 is a perspective view of an embodiment of the sloped basin with a footrest coupled thereto.
Figure 9:
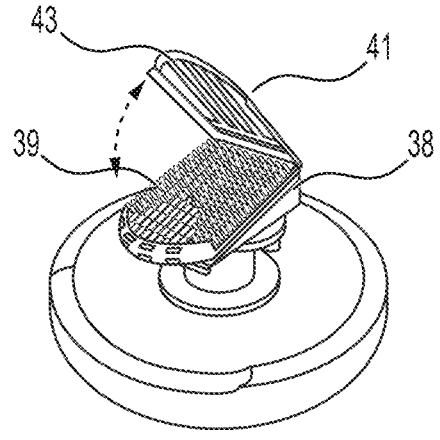
FIG. 9 is a perspective view of an embodiment of the sloped basin with a footrest coupled thereto and a scrubber pad positioned inside the footrest.
Figure 10:
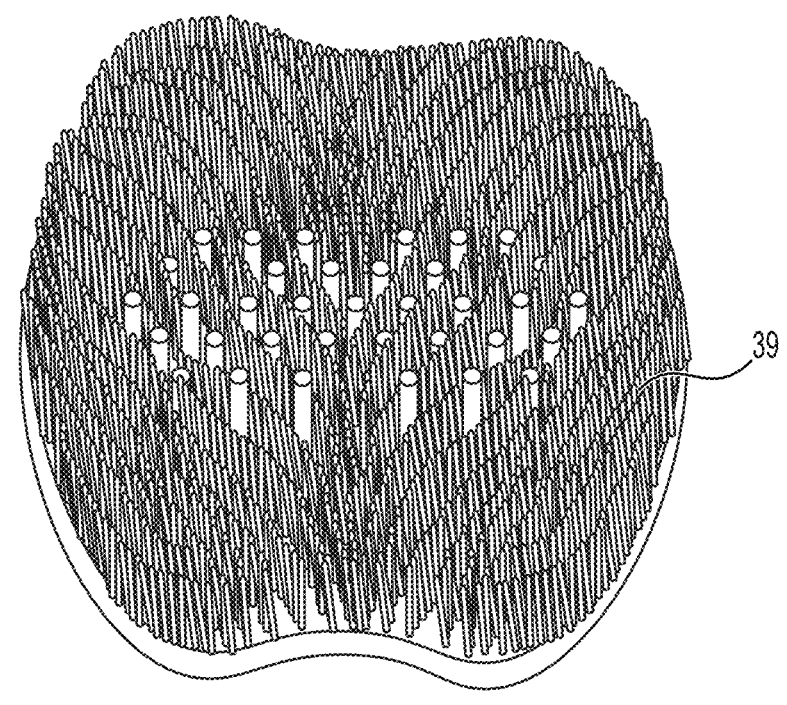
FIG. 10 is a top view of an embodiment of a scrubber pad.

The footrest 38 can be coupled to the sloped basin 16, as illustrated in FIGS. 6, 8, and 9. In an embodiment, the footrest 38 is mechanically coupled to a floor 40 of the sloped basin 16. The footrest 38 may include a footrest housing with a lid 41 that has openings 43 defined therethrough. A scrubbing mat 39 may be disposed in the footrest housing. In various embodiments, the footrest 38 may be configured to move using the first set of controls 24 in order to scrub the foot of a user with the scrubbing mat 39. For example, the footrest 38 may move in a front to back motion to scrub the foot of the user. In still other embodiments, the footrest 38 may be stationary. The scrubbing mat 39, as illustrated in FIG. 10, may be placed under the lid 41 of the footrest 38. The scrubbing mat 39 may extend through openings 43 in the lid 41 of the footrest 38. In various embodiments additional scrubbers may be included in the apparatus housing proximate the footrest. The additional scrubbers may be on the sides of the footrest in various embodiments. In other embodiments, there may be additional scrubber above the footrest. Scrubbers above the footrest may be moved closer to the footrest by the user using a control system. In still other embodiments, additional scrubbers may be both on the sides and above the footrest.

Referring to FIG. 2, a method of sanitizing the foot sink may include a cycle of water, soap, air, then UV light to sanitize the inside of the foot sink area. The sanitizing cycle may be started by a user by pressing the third button 54 proximate a top end of the apparatus housing. The status of the cleaning process may be shown on a screen 55. In various embodiments, the screen may show icons depicting the steps in the sanitizing cycle such as water, soap, air, and UV light. The screen may also show a timer for the length of the sanitizing cycle. The timer may count up or down to show how much time is left in the cleaning process. In various embodiments, the sanitizing cycle may be at least about 5 minutes. In other embodiments, the sanitizing cycle may be more or less than 5 minutes.

Figure 3:
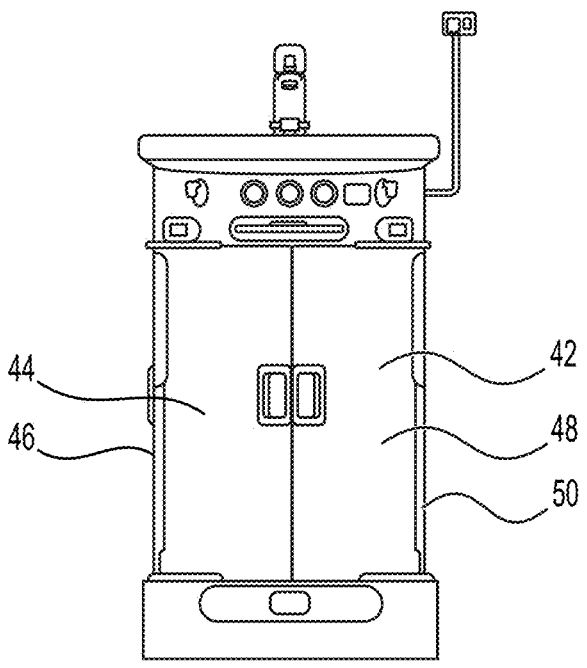
FIG. 3 is a front view of an embodiment of a hand and foot sink apparatus having a generally rectangular apparatus housing, with closed doors.
Figure 4:
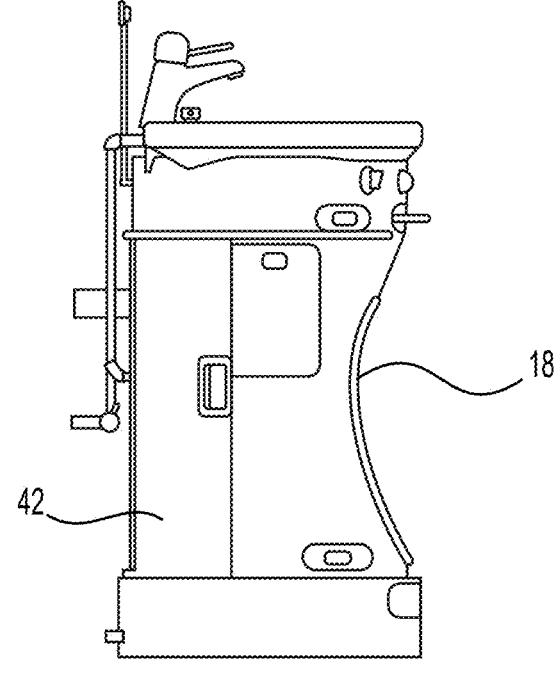
FIG. 4 is a side view of an embodiment of the hand and foot sink apparatus shown in FIG. 3, with the doors open.
Figure 5:
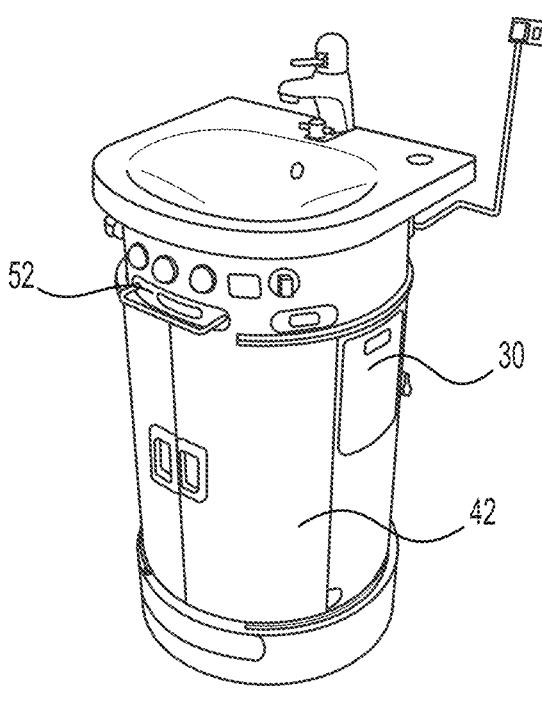
FIG. 5 is a perspective view of an embodiment of a hand and foot sink apparatus with a generally round apparatus housing and doors closed.

Referring to FIGS. 3, 4, and 5, the apparatus housing 8 may include pivotable doors 42. The doors can include left door 44 coupled with a left side 46 of the apparatus housing 8 and right door 48 coupled with a right side 50 of the apparatus housing 8. The doors 42 are configured to selectively cover the opening 18 of the apparatus housing 8. In various embodiments, the doors 42 may slide on a track to open and close, as illustrated in FIG. 4. In other embodiments, the doors 42 may be hingedly coupled with the apparatus housing and open on a pivot.

In various embodiments, the first set of controls 24 and the second set of controls 26 are buttons automatically configured to control the footrest and the nozzles, respectively. As described herein, automatically may include electronic controls. In other embodiments, the first set of controls 24 and the second set of controls 26 may include knobs, buttons, or switches configured to manually operate the footrest and the nozzles.

In other embodiments, the apparatus housing 8 may include UV lights 52 and a third set of controls 54 configured to operate the UV lights 52. The UV lights may be part of a sanitizing cycle as previously described. As illustrated in FIG. 1, UV light 52 can be disposed within the apparatus housing 8 under the hand sink 4. In an embodiment, the UV lights 52 may be configured to illuminate the foot sink 6. In an embodiment, the UV lights 52 may be used for disinfecting the foot sink 6. In various embodiments, the UV lights 52 may be activated when the doors of the foot sink 6 are closed. In another embodiment, the UV lights may be activated a user with a third set 54 of controls. In still another embodiment, the UV lights may be part of a cleaning and sanitizing routine.

The UV light source may include any type of ultraviolet light capable of destroying bacterial microbes such as, but not limited to, UV-C light which has a wavelength of 200-280 nm and is highly effective in killing bacteria, viruses and fungi.

In an embodiment, the apparatus housing 8 includes one or more air blowers for washing the hands or feet of the user. In an embodiment, a first pair of blowers 56 can be positioned near a top edge of the apparatus housing 8 and a second pair of blowers 58 can be positioned near a bottom edge of the apparatus housing 8 for drying feet of a user, as illustrated in FIG. 2. The blowers 56 and 58 can be electrically coupled with the second set of controls 26 proximate a top edge 26 of the apparatus housing 8. The second set of controls 26 can be configured for operating the blowers.

Although not depicted in the figures, the apparatus housing can include a drainpipe connected to the drain, an air dryer pipe connected to the blowers, and a water pipe connected to the faucet and the sprayers. Additionally, the apparatus housing can include a compartment which includes instruments known in the art for operating faucets, sprayers, and blowers upon manipulating the appropriate controls of the electrical control systems as well as operating equipment, including, an electric water pump, pipes, valves, fittings and electric hot air dryer.

Figure 11:
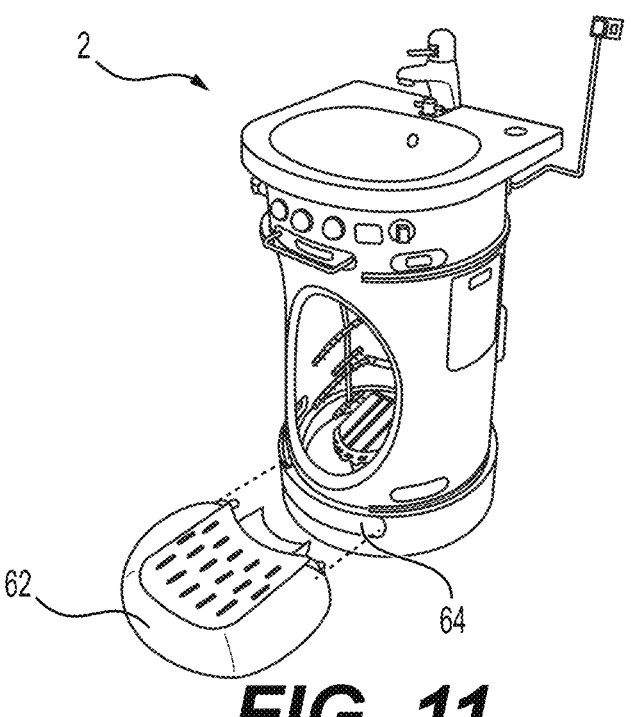
FIG. 11 is a perspective view of an embodiment of a hand and foot sink apparatus with a removable footrest.

Referring to FIG. 11, the apparatus housing 8 may include a removable footrest 62. As illustrated, the removable footrest 62 is removably positioned within a second opening 64 in the apparatus housing 8 under the foot sink 6 of the apparatus housing 8. In various embodiments, the removable footrest 62 may be formed from any suitable material, such as a material selected from the group consisting of plastic, silicone, rubber, and acrylic. The removable footrest 62 can be removed from the apparatus housing 8 and placed on the floor so that feet of a user may be placed thereon after washing to prevent the floor from getting wet.

Figure 12:
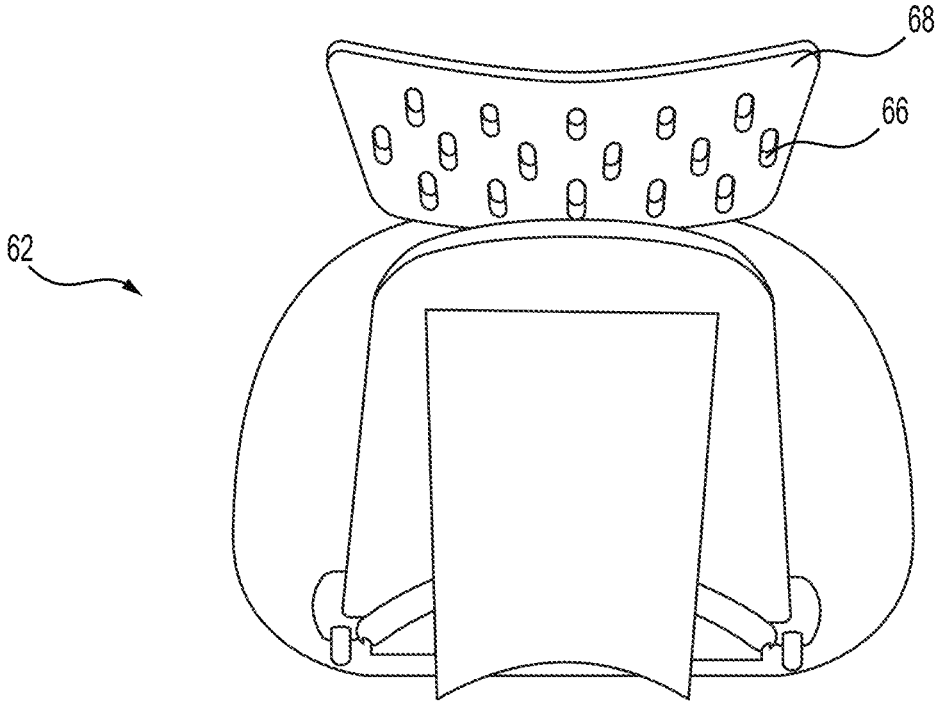
FIG. 12 is a front view of an embodiment of a removable footrest with the top open.

Referring to FIG. 12, the removable footrest 62 may have a footrest housing with a lid 68 that can be opened to allow cleaning of the removable footrest housing. The removable footrest housing of the removable footrest 62 can be slanted to allow water from the foot of a user to drain back into the drain of the foot sink. Water from the foot of the user may drip through holes 66 in the lid 68 of the removable footrest 62.

It will be understood that the hand and foot sink apparatus is not limited to the specific embodiments described above, but encompasses any and all embodiments within the scope of the generic language of the following claims enabled by the embodiments described herein, or otherwise shown in the drawings described above in terms sufficient to enable one of ordinary skill in the art to make and use the claimed subject matter.

What is claimed is:

1. A hand and foot sink apparatus, comprising:
an apparatus housing having a top end and a bottom end, the apparatus housing including:
a hand sink disposed at the top end of the apparatus housing, the hand sink including a basin, a faucet, and a drain,
a foot sink disposed within a first opening along a side portion of the apparatus housing below the hand sink, the foot sink being partially enclosed within the apparatus housing and including a basin, a plurality of sprayers, and a footrest, the footrest being disposed in the basin;
one or more nozzles configured to dispense soap;
one or more supply holders, each of the supply holders configured to store one or more containers of soap, the one more containers of soap being connected to the one or more nozzles through conduits;
one or more controls configured to operate the one or more nozzles; and
a removable footrest positioned within a second opening of the housing under the foot sink, wherein the removable footrest is configured to drain into the foot sink.

2. The apparatus of claim 1, wherein the footrest is mechanically coupled to a floor of the basin of the foot sink and the footrest is configured to move to scrub the foot of a user.

3. The apparatus of claim 2, wherein the footrest includes a footrest housing with a lid, the lid being configured to selectively cover an opening of the footrest housing.

4. The apparatus of claim 1, wherein the first opening of the apparatus housing is curved inward, and the basin is sloped.

5. The apparatus of claim 4, wherein the apparatus housing further comprises two doors configured to selectively cover the first opening of the housing.

6. The apparatus of claim 1, wherein the apparatus housing further comprises one or more UV lights.

7. The apparatus of claim 1, wherein the apparatus housing further comprises a first pair of blowers proximate the top end of the apparatus housing under the hand sink and a second pair of blowers proximate the foot sink and below the first pair of blowers, the blowers being electrically coupled to a third set of controls.

8. A hand and foot sink apparatus, comprising:
an apparatus housing having a top end and a bottom end, the apparatus housing including:
a hand sink disposed at the top end of the apparatus housing, the hand sink including a basin, a faucet, and a drain,
a foot sink disposed within a first opening along a side portion of the apparatus housing below the hand sink, the foot sink being partially enclosed within the apparatus housing and including a basin, a plurality of sprayers, and a footrest, the footrest being disposed in the basin, wherein the footrest includes a footrest housing having a lid with openings defined therethrough, the lid being configured to selectively close the housing;
one or more nozzles configured to dispense soap;
one or more supply holders, each of the supply holders configured to store the one or more containers of soap, the one more containers of soap being connected to the one or more nozzles through conduits;
a first pair of blowers proximate the top end of the apparatus housing and under the hand sink;
one or more UV lights directed toward the foot sink; and
one or more controls configured to operate the one or more nozzles, and the first pair of blowers.

9. The apparatus of claim 8, wherein the one or more UV lights are electrically coupled with a driver circuit for powering the ultraviolet light source.

10. The apparatus of claim 8, further comprising a second pair of blowers below the first pair of blowers and proximate the foot sink, the second pair of blowers being operated by the one or more controls.

11. The apparatus of claim 8, wherein the footrest is mechanically coupled to a floor of the basin and includes a motor, and the footrest is configured to move to scrub foot of a user.

12. The apparatus of claim 8, further comprising two doors, wherein one door is coupled with a left side of the apparatus housing and a second door is coupled with a right side of the apparatus housing, the doors being configured to selectively cover the first opening in the apparatus housing.

13. The apparatus of claim 8, further comprising a removable footrest removably secured within a second opening in the housing and under the foot sink.

14. A hand and foot sink apparatus, comprising:
an apparatus housing having a top end and a bottom end, the housing including
a hand sink disposed at the top end of the apparatus housing, the hand sink including a basin, a faucet, and a drain,
a foot sink disposed within a first opening along a side portion of the apparatus housing below the hand sink, the foot sink being partially enclosed within the apparatus housing and including a basin, a plurality of sprayers, and a footrest, the footrest being disposed in the basin;
one or more nozzles configured to dispense soap;
one or more supply holders, each of the supply holders configured to store the one or more containers of soap, the one more containers of soap being connected to the one or more nozzles through conduits;
a footrest mechanically secured to the basin of the foot sink, the footrest including a footrest housing having a lid with openings defined therethrough, the lid being configured to selectively close the footrest housing;

a removable footrest removably secured within a second opening of the apparatus housing and below the foot sink;

a first pair of blowers proximate the top end of the apparatus housing and under the hand sink;

a second pair of blowers proximate the foot sink and below the foot sink; and one or more controls configured to operate the one or more nozzles and the blowers.

* * * * *